(12) United States Patent
Haam et al.

(10) Patent No.: US 10,487,207 B2
(45) Date of Patent: Nov. 26, 2019

(54) BIOENVIRONMENT-SENSITIVE NANOPARTICLE COMPRISING POLYMER HAVING COMPLEMENTARY CHARGES

(71) Applicant: University-Industry Foundation, Yonsei University, Seoul (KR)

(72) Inventors: Seungjoo Haam, Seoul (KR); Yong-min Huh, Seoul (KR); Hyun-Ouk Kim, Seoul (KR); Jihye Choi, Incheon (KR); Eunji Jang, Seoul (KR); Byunghoon Kang, Seoul (KR); Ilkoo Noh, Seoul (KR); Seungmin Han, Seoul (KR); Seung Won Song, Seoul (KR); Hwunjae Lee, Seoul (KR); Haejin Chun, Seoul (KR)

(73) Assignee: University-Industry Foundation, Yonsei University, Seoul (KR)

( * ) Notice: Subject to any disclaimer, the term of this patent is extended or adjusted under 35 U.S.C. 154(b) by 539 days.

(21) Appl. No.: 14/629,718

(22) Filed: Feb. 24, 2015

(65) Prior Publication Data

US 2015/0376405 A1    Dec. 31, 2015

(30) Foreign Application Priority Data

Jun. 25, 2014 (KR) .................. 10-2014-0078112

(51) Int. Cl.
| | | |
|---|---|---|
| C08L 79/02 | (2006.01) | |
| G01N 1/30 | (2006.01) | |
| A61K 47/34 | (2017.01) | |
| A61K 9/127 | (2006.01) | |

(52) U.S. Cl.
CPC ............ *C08L 79/02* (2013.01); *A61K 9/1273* (2013.01); *G01N 1/30* (2013.01); *C08L 2203/02* (2013.01); *C08L 2205/025* (2013.01)

(58) Field of Classification Search
None
See application file for complete search history.

(56) References Cited

U.S. PATENT DOCUMENTS

| | | | | |
|---|---|---|---|---|
| 6,204,247 B1* | 3/2001 | Gegg | ................... | C07K 1/1077 514/5.8 |
| 2005/0215438 A1* | 9/2005 | Prud'homme | ........... | C09K 8/12 507/117 |
| 2012/0135070 A1 | 5/2012 | Kros et al. | | |
| 2016/0000725 A1* | 1/2016 | Geilich | ................... | A61K 31/43 424/497 |

FOREIGN PATENT DOCUMENTS

| | | | |
|---|---|---|---|
| CN | 101565497 | * | 5/2009 |
| CN | 101912624 | * | 6/2010 |
| CN | 101912624 | | 12/2010 |
| EP | 2087912 | | 8/2009 |

OTHER PUBLICATIONS

Shixian et al. Charge-Conversational PEG-Polypeptide Polyionic Complex Nanoparticles from Simple Blending of a Pair of Oppositely Charged Block copolymers and an Intelligent Vehicle for Efficient Antitumor Drug Delivery.*
Yildiz et al. "Real-time determination of the activity of ATPase by use of a watersoluble polythiophene".*
European Search Report and the European Search Opinion dated Oct. 22, 2015 From the European Patent Office Re. Application No. 15173789.7.
Harada et al. "Effect of Charged Segment Length on Physicochemical Properties of Core-Shell Type Polyion Complex Micelles From Block Ionomers", Macromolecules, XP055220569, 36(13): 4995-5001, Published on Web May 31, 2003. Abstract, p. 4996, First 2 Paras.
Lin et al. "Design of an Amphiphilic Polymer for Nanoparticle Coating and Functionalization", Small, XP002692454, 4(3): 334-341, Mar. 3, 2008. p. 340, 1-h Col., 2nd Para.
Yildiz et al. "Real-Time Determination of the Activity of ATPase by Use of Water-Soluble Polythiophene", Analytical and Bioanalytical Chemistry, XP035127407, 404(8): 2369-2375, Published Online Sep. 4, 2012. Abstract.

* cited by examiner

*Primary Examiner* — Jeffrey T. Palenik
*Assistant Examiner* — Danah Al-Awadi

(57) ABSTRACT

A bioenvironment-sensitive nanoparticle including a polymer having complementary charges, a method of manufacturing the same, and a pharmaceutical use of the bioenvironment-sensitive nanoparticle are disclosed. The bioenvironment-sensitive nanoparticle can be useful in stably and effectively delivering a target material such as a drug even when used at a small quantity since the nanoparticle is stable in extracellular environments. Also, the bioenvironment-sensitive nanoparticle can be useful in selectively diagnosing or treating cancer cells since the nanoparticle is specific to environments of the cancer cells.

23 Claims, 7 Drawing Sheets

Figure 1:
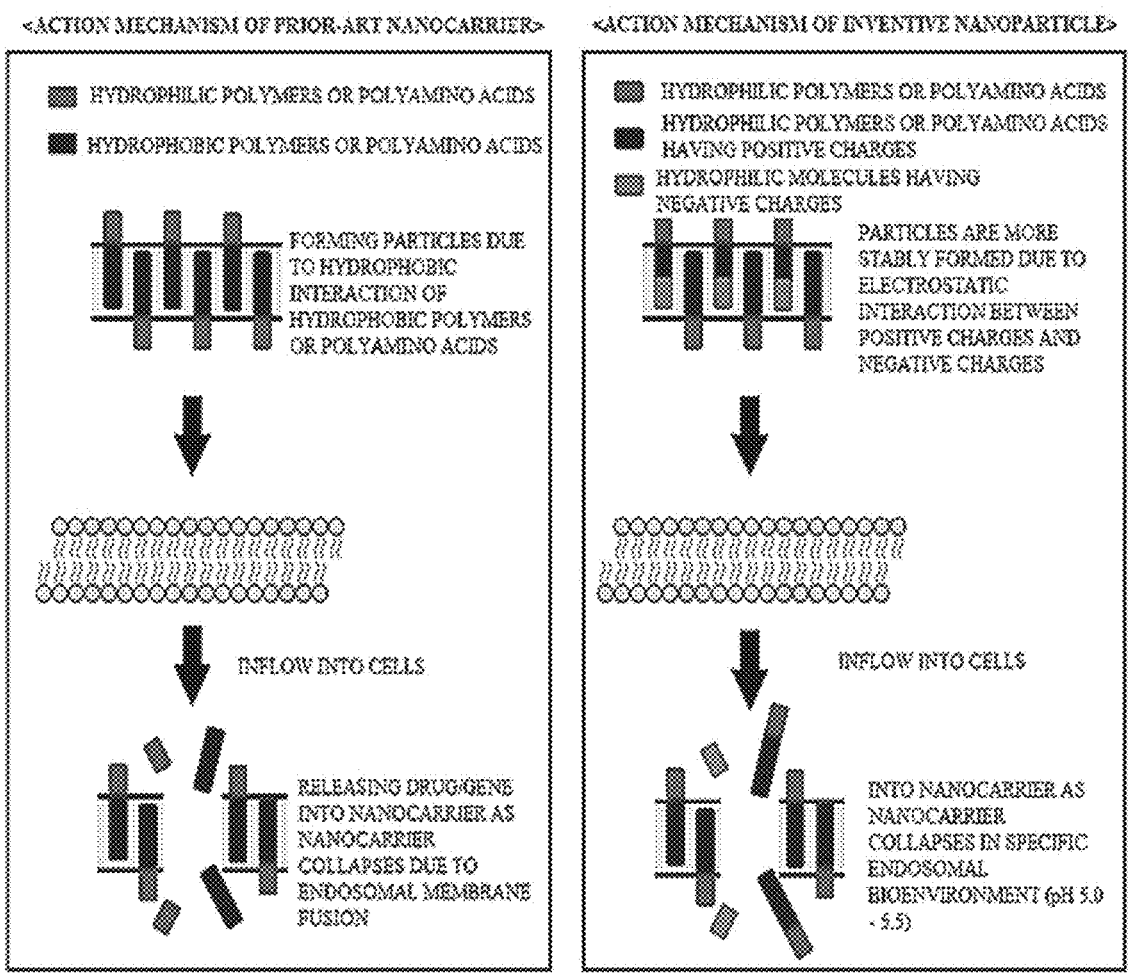

(1 of 7 Drawing Sheet(s) Filed in Color)

BIOENVIRONMENT-SENSITIVE NANOPARTICLE COMPRISING POLYMER HAVING COMPLEMENTARY CHARGES

RELATED APPLICATION

This application claims the benefit of priority of Korean Patent Application No. 10-2014-0078112 filed Jun. 25, 2014, the contents of which are incorporated herein by reference in their entirety.

BACKGROUND OF INVENTION

The present invention relates to a bioenvironment-sensitive nanoparticle including a polymer having complementary charges, a method of manufacturing the same, and a pharmaceutical use of the bioenvironment-sensitive nanoparticle.

Generally, a nanocarrier for delivering a target material such as a drug is manufactured according to the hydrophobic interaction of a hydrophobic polymer. The term "hydrophobic interaction" refers to an interaction in which non-polar groups (i.e., hydrophobic groups) having low affinity to water molecules join together in an aqueous solution.

However, such a method has a problem in that non-specific interactions occur in extracellular environments (U.S. Patent Application Publication No. 2012-0135070).

BRIEF SUMMARY OF THE INVENTION

The present invention is designed to solve the problems of the prior art, and therefore it is an object of the present invention to provide a bioenvironment-sensitive nanoparticle capable of being maintained in a stable state until the nanoparticle is delivered into cells since the use of electrostatic attractions between positive charges and negative charges cause no non-specific interactions in extracellular environments.

According to an aspect of the present invention, there is provided a nanoparticle including a block copolymer (I) having positive charges, and a block copolymer (II) having negative charges. Here, the block copolymer (I) contains a hydrophilic polymer and a polymer having positive charges as repeating units;

the block copolymer (II) contains a hydrophilic polymer and a polymer, to which an acid radical having a negative charge is bound via an amide bond, as repeating units;

the polymer to which the acid radical having a negative charge is bound via the amide bond contains a polymer containing a functional group capable of forming an amide bond, and an acid radical having a negative charge bound thereto via the amide bond; and the block copolymers (I) and (II) form a self-assembly by means of the balance between the positive charges and the negative charges.

According to another aspect of the present invention, there is provided a method of manufacturing the bioenvironment-sensitive nanoparticle defined in claim 1, which includes reacting a block copolymer (I) and a block copolymer (II). Here, the block copolymer (I) contains a hydrophilic polymer and a polymer having positive charges as repeating units;

the block copolymer (II) contains a hydrophilic polymer and a polymer, to which an acid radical having a negative charge is bound via an amide bond, as repeating units; and the polymer to which the acid radical having a negative charge is bound via the amide bond contains a polymer containing a functional group capable of forming an amide bond, and an acid radical having a negative charge bound thereto via the amide bond.

According to still another aspect of the present invention, there is provided a target-directed contrast agent composition including the bioenvironment-sensitive nanoparticle.

According to yet another aspect of the present invention, there is provided a composition for analyzing the activity or quantity of ATP, which includes the bioenvironment-sensitive nanoparticle.

The nanoparticle according to one exemplary embodiment of the present invention can be useful in stably and efficiently delivering a target material such as a drug even when used at a small quantity since the nanoparticle is stable in extracellular environments.

Also, the nanoparticle according to one exemplary embodiment of the present invention can be useful in selectively diagnosing or treating cancer cells since the nanoparticle is specific to environments of the cancer cells.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

These and other features, aspects, and advantages of preferred embodiments of the present invention will be more fully described in the following detailed description, taken in conjunction with the accompanying drawings.

Figure 2:
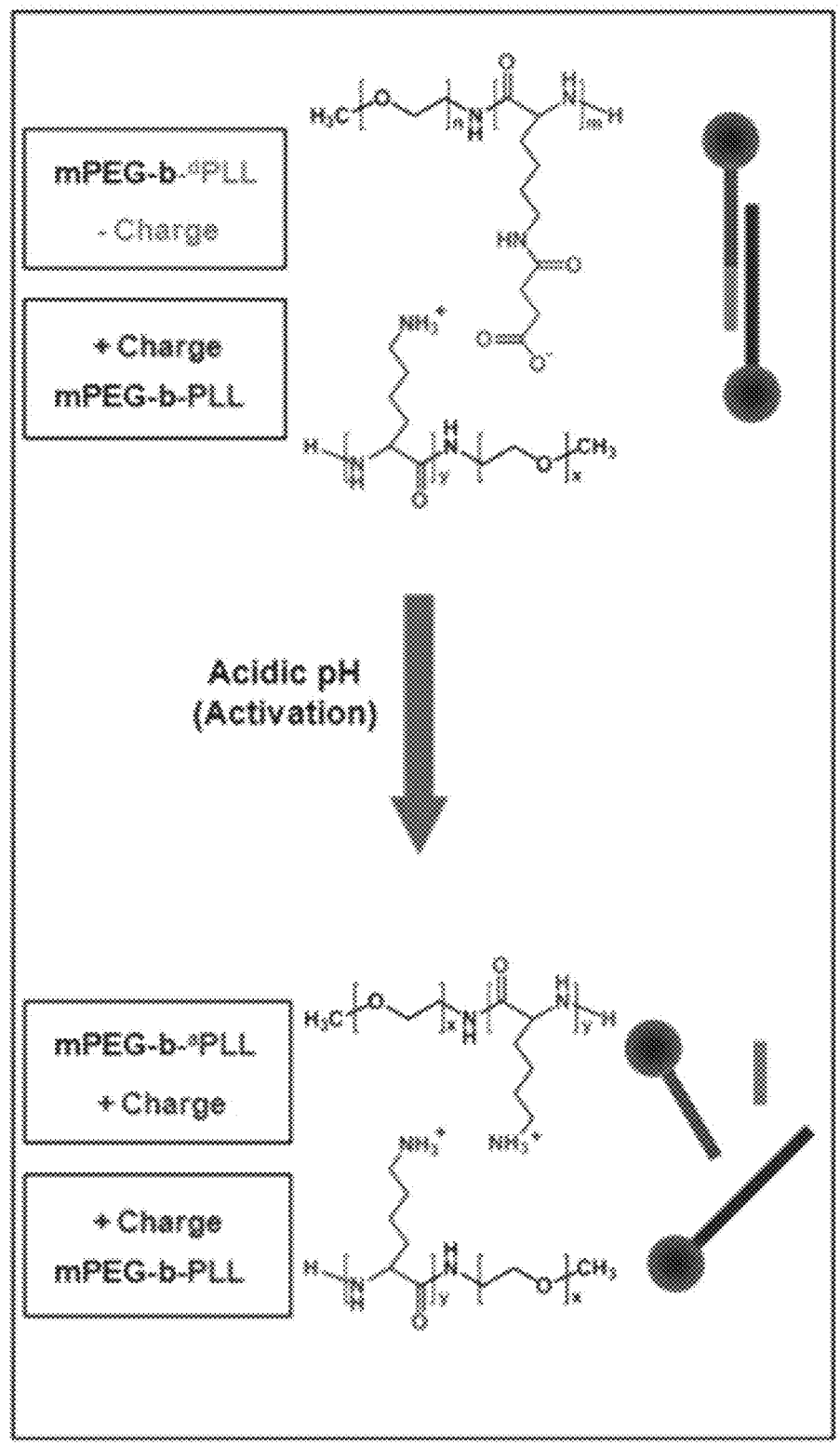
Figure 3:
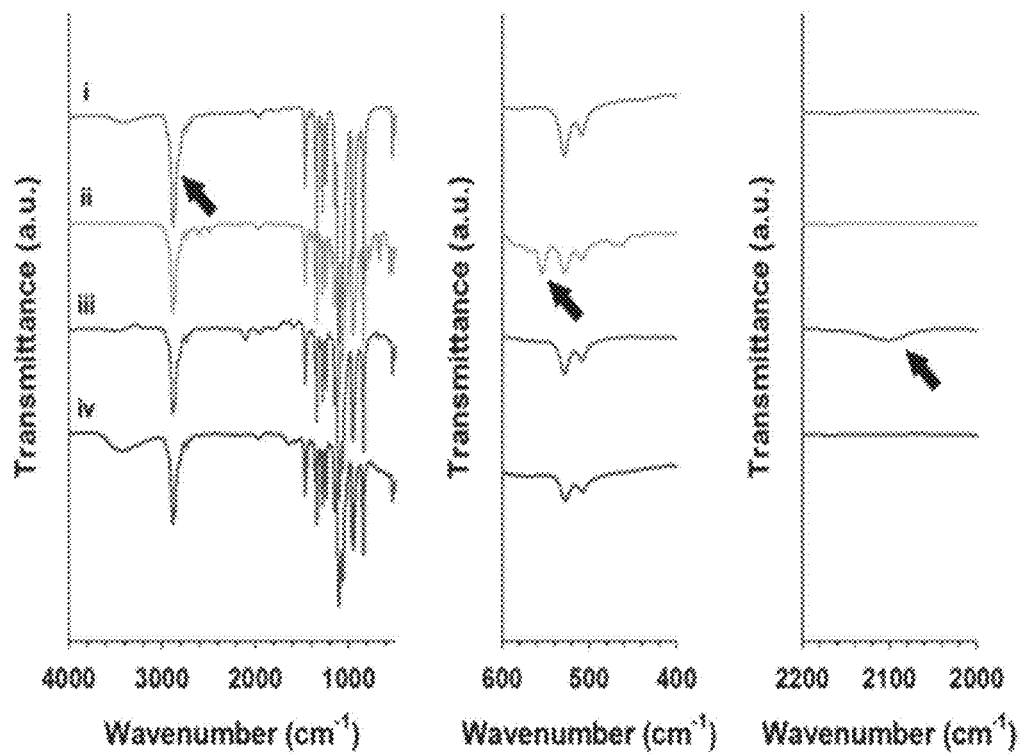
Figure 4:
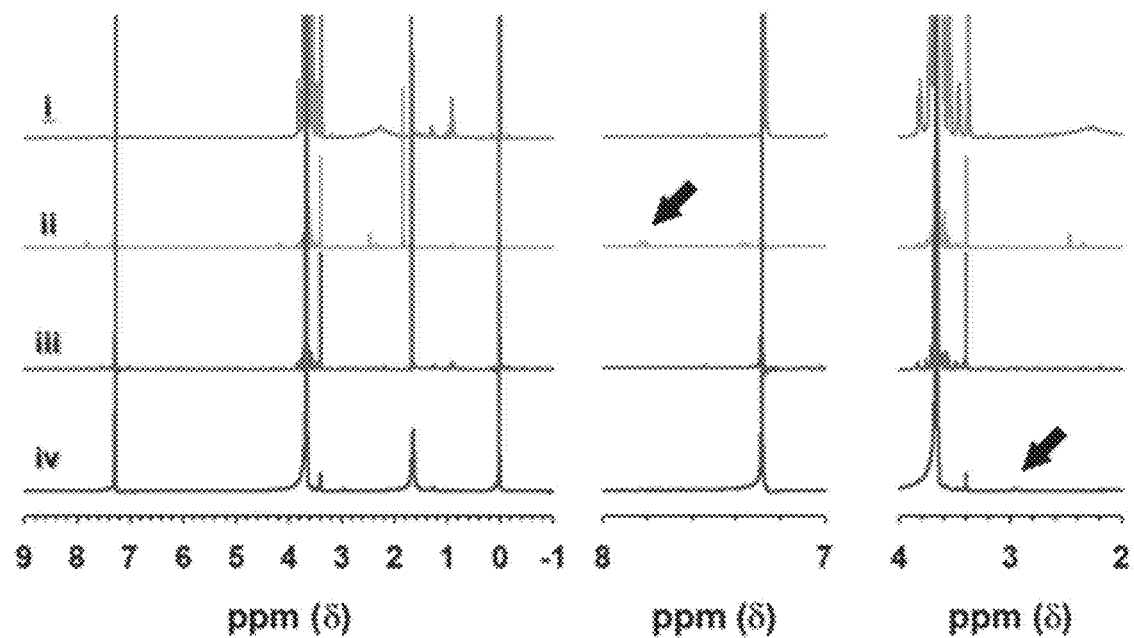
Figure 5:
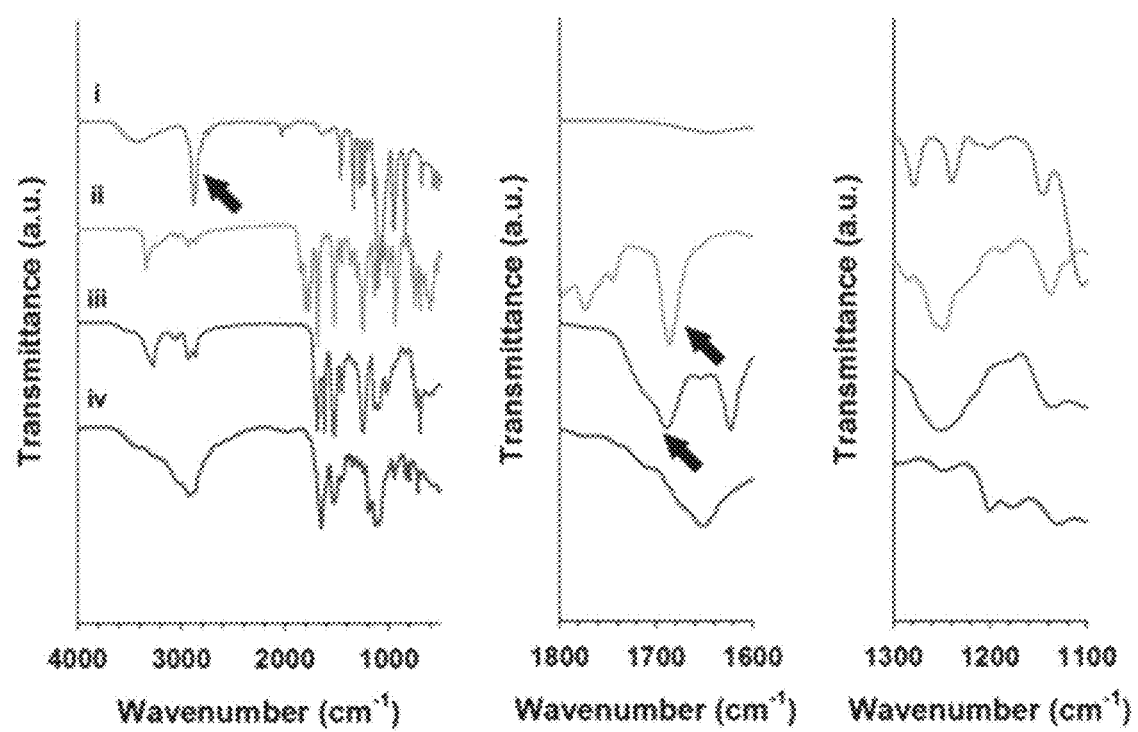
Figure 6:
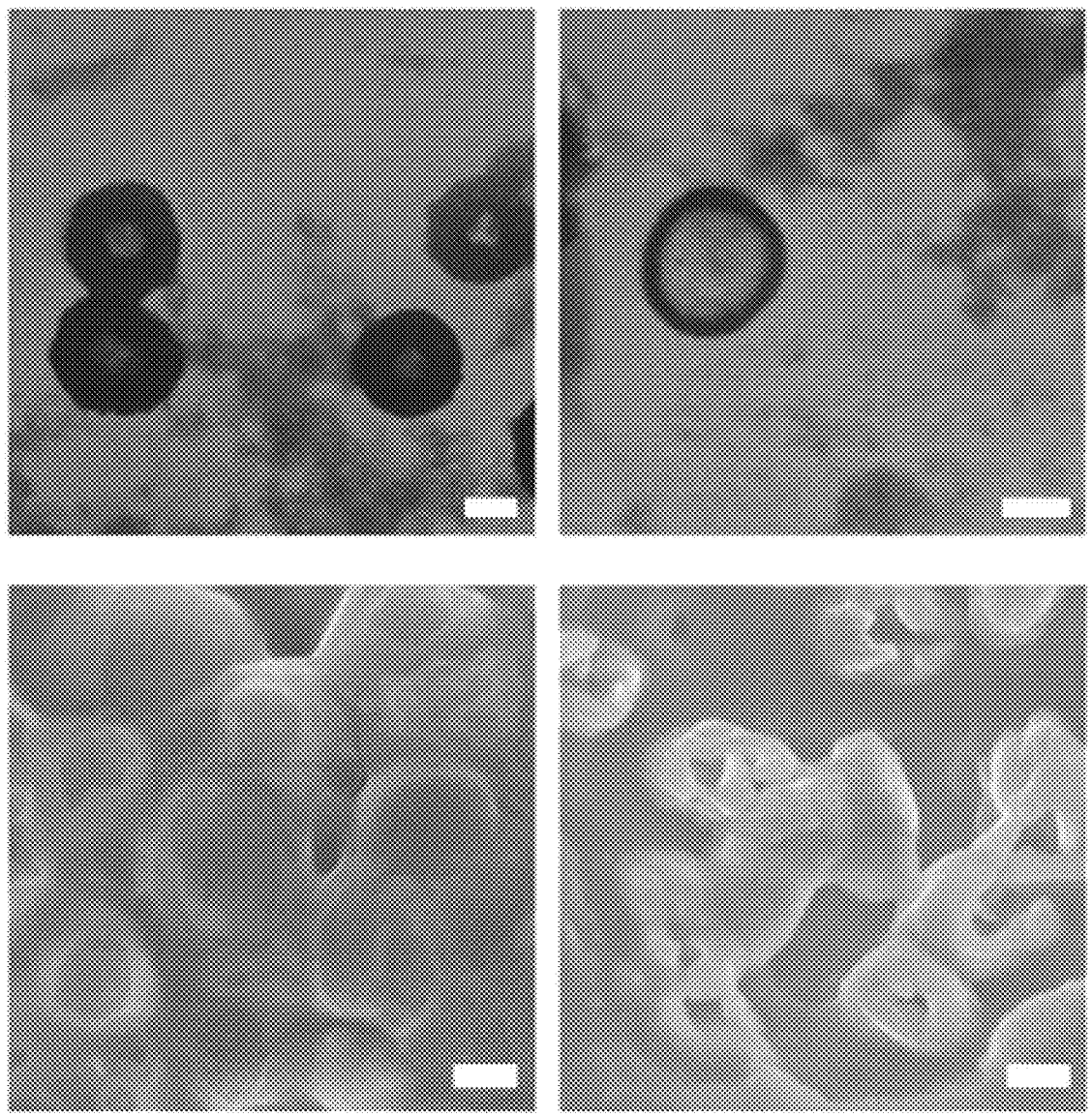
Figure 7:
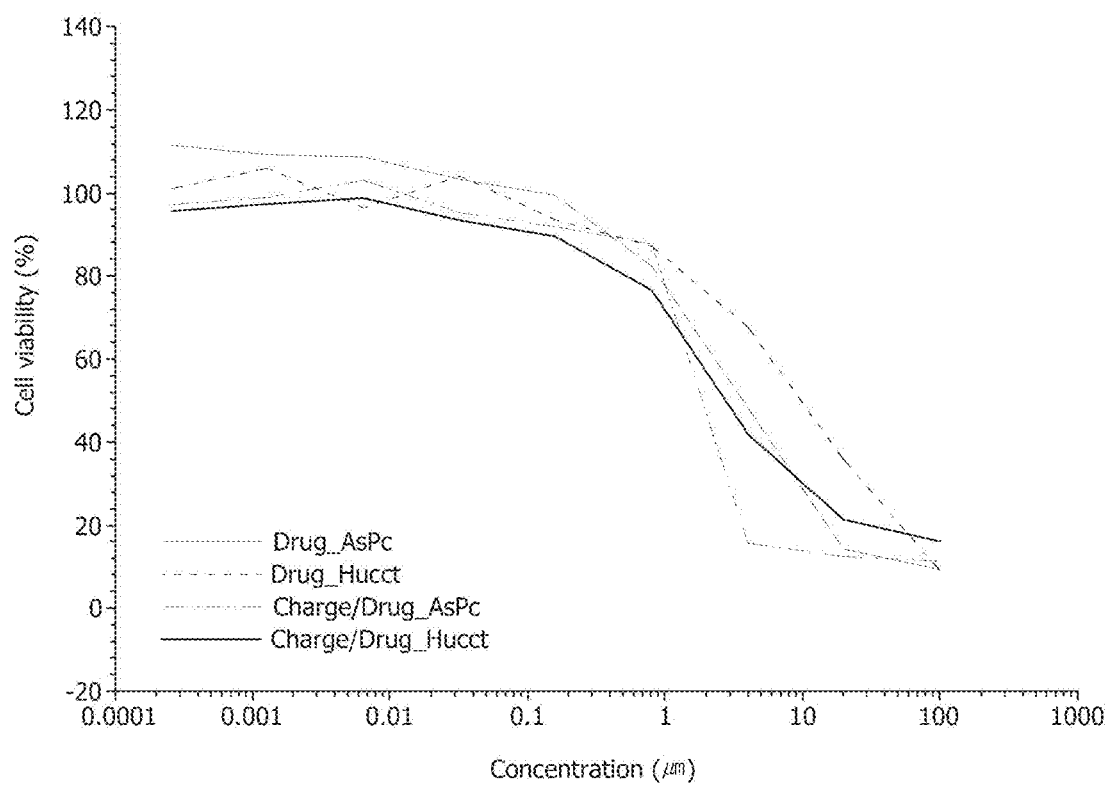
Figure 8:
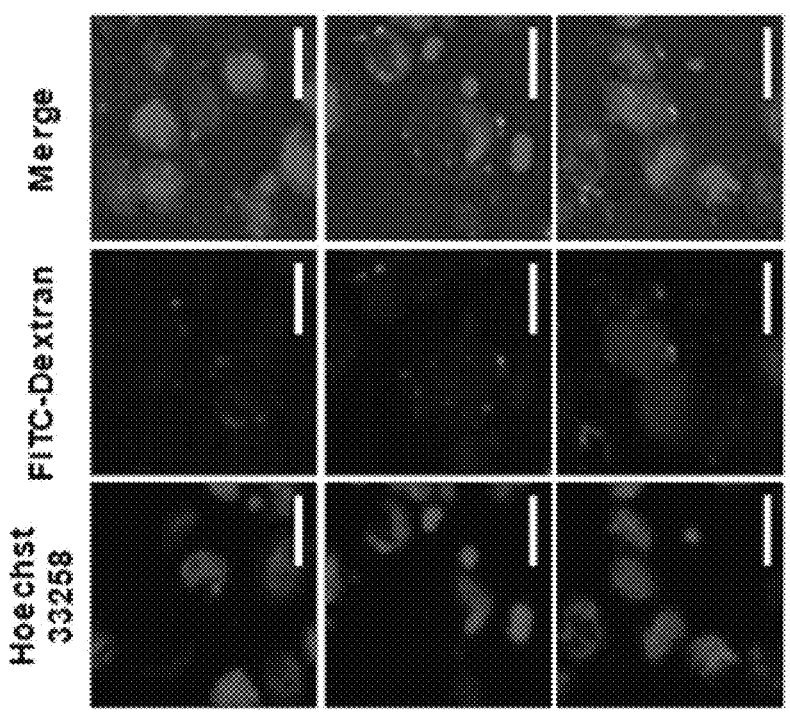
Figure 8:
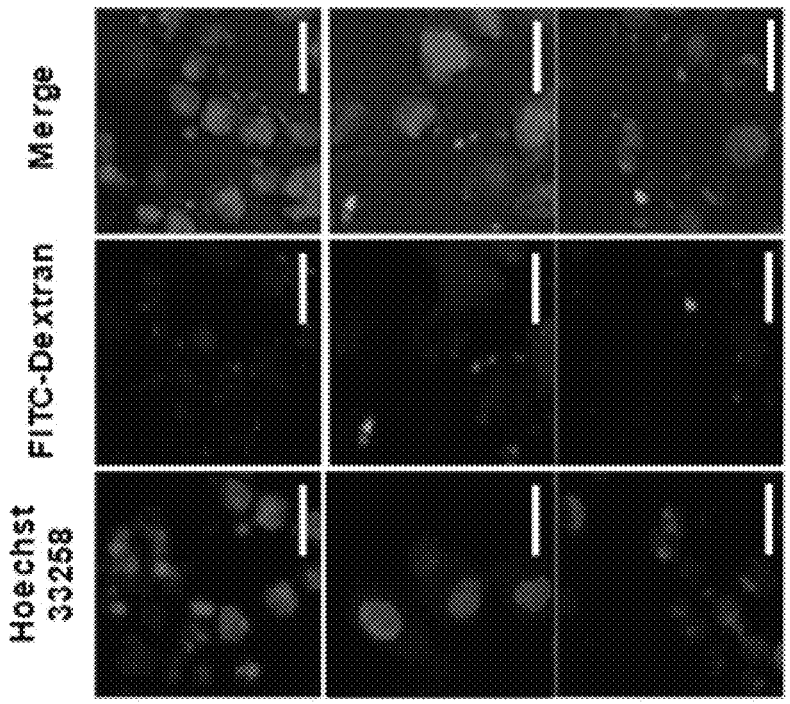

In the drawings:

FIG. 1 is a diagram showing the action mechanisms of a conventional nanocarrier and a bioenvironment-sensitive nanoparticle according to one exemplary embodiment of the present invention;

FIG. 2 is a schematic diagram showing a block copolymer (I) containing a hydrophilic polymer and a polymer having positive charges as repeating units and a block copolymer (II) containing a hydrophilic polymer and a polymer, to which an acid radical having a negative charge is bound via an amide bond, as repeating units (an upper panel) to manufacture the bioenvironment-sensitive nanoparticle according to one exemplary embodiment of the present invention, and showing the inflow of the bioenvironment-sensitive nanoparticle according to one exemplary embodiment of the present invention into cells and the selective collapse of the bioenvironment-sensitive nanoparticle in a tumor microenvironment (a lower panel);

FIG. 3 is a diagram showing the Fourier transform-infrared spectroscopy (FT-IR) results determined in a process of modifying mPEG-OH into mPEG-NH$_2$ (mPEG-OH→mPEG-TsCl→mPEG-N$_3$→mPEG-NH$_2$), that is, showing the FT-IR results of (i) mPEG, (ii) mPEG-TsCl, (iii) mPEG-N$_3$, and (iv) mPEG-NH$_2$: A peak at 2,850 cm$^{-1}$ represents CH$_3$ of mPEG (indicated by an arrow in a left panel), a peak at 560 cm$^{-1}$ represents S—O of mPEG-TsCl (indicated by an arrow in a middle panel), and a peak at 2,103 cm$^{-1}$ represents N$_3$ of mPEG-N$_3$ (indicated by an arrow in a right panel);

FIG. 4 is a diagram showing the $^1$H-NMR results determined in a process of modifying mPEG-OH into mPEG-NH$_2$ (mPEG-OH→mPEG-TsCl→mPEG-N$_3$→mPEG-NH$_2$), that is, showing the $^1$H-NMR results of (i) mPEG, (ii) mPEG-TsCl, (iii) mPEG-N$_3$, and (iv) mPEG-NH$_2$: Peaks at 7.79 and 7.49 ppm represent 2H of TsCl (indicated by an arrow in a middle panel), and a peak at 2.90 ppm represents $CH_2$—$NH_2$ of mPEG-$NH_2$ (indicated by an arrow in a right panel);

FIG. 5 is a diagram showing the FT-IR results determined for the bioenvironment-sensitive nanoparticle according to one exemplary embodiment of the present invention, that is, showing the FT-IR results of (i) mPEG-$NH_2$, (ii) Lys-NCA, (iii) mPEG-b-pLys(z), and (iv) mPEG-b-pLys: A peak at 2,850 $cm^{-1}$ represents $CH_3$ (indicated by an arrow in a left panel), a peak at 1,650 $cm^{-1}$ represents amide I of Lys-NCA (indicated by an arrow in a middle panel), and a peak at 1,710 $cm^{-1}$ represents Z of mPEG-pLys(Z);

FIG. 6 shows TEM and SEM images of the shapes of polymersomes in the bioenvironment-sensitive nanoparticle according to one exemplary embodiment of the present invention (scale bar; 100 nm);

FIG. 7 is a diagram showing a cytotoxicity effect of the bioenvironment-sensitive nanoparticle according to one exemplary embodiment of the present invention in biliary tract cancer cell lines ASPC and Hucct-1: In the drawing, a Drug_AsPc represents a case in which only a drug is applied in ASPC, a Drug_Hucct represents a case in which only the drug is applied in Hucct-1, a Charge/Drug_AsPc represents a case in which a drug carried by the nanoparticle according to one exemplary embodiment of the present invention is applied in ASPC, and a Charge/Drug_Hucct represents a case in which the drug carried by the nanoparticle according to one exemplary embodiment of the present invention is applied in Hucct-1; and FIG. 8 is a diagram showing the results obtained by determining levels of inflow of the FITC-loaded bioenvironment-sensitive nanoparticle according to one exemplary embodiment of the present invention into cells in the biliary tract cancer cell lines ASPC and Hucct-1.

DETAILED DESCRIPTION OF THE INVENTION

These and other advantages and features of the present invention and method of achieving them will be apparent from the following description of preferred embodiments, with reference to the accompanying drawings. However, the present invention is not limited to the following embodiments but will be embodied in various forms. That is, the embodiments of the present invention play a role of making the disclosure of the present invention perfect, and are provided to inform a person who has an ordinary knowledge and skill in the art to which this invention belongs of the scope of the invention. This invention should be defined based on the scope of claims.

The terms disclosed below are terms defined in consideration of their functions in the present invention, and thus may be differently defined according to users, operators' intensions, and practices. Therefore, the definitions of the terms should be given based on the contents throughout this specification.

The present invention provides a nanoparticle including a block copolymer (I) having positive charges, and a block copolymer (II) having negative charges. Here, the block copolymer (I) contains a hydrophilic polymer and a polymer having positive charges as repeating units, the block copolymer (II) contains a hydrophilic polymer and a polymer, to which an acid radical having a negative charge is bound via an amide bond, as repeating units, the polymer to which the acid radical having a negative charge is bound via the amide bond contains a polymer containing a functional group capable of forming an amide bond, and an acid radical having a negative charge bound thereto via the amide bond, and the block copolymers (I) and (II) form a self-assembly by means of the balance between the positive charges and the negative charges.

In this specification, the term "acid radical" refers to a negative ion in which $H^+$ is removed from an acid.

According to one exemplary embodiment, the block copolymer (I) of the present invention may be represented by the following Formula 1.

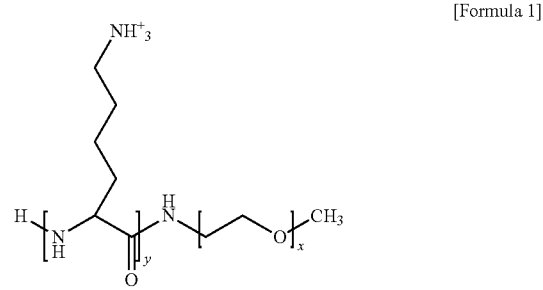

[Formula 1]

In Formula 1, x represents an integer ranging from 25 to 110, and y represents an integer ranging from 13 to 55.

According to one exemplary embodiment, the block copolymer (II) of the present invention may be represented by the following Formula 2.

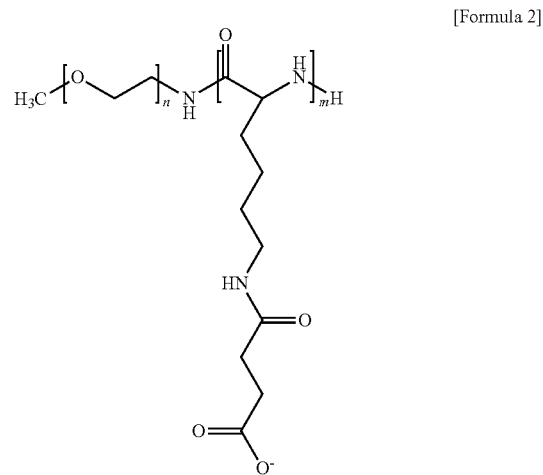

[Formula 2]

In Formula 2, n represents an integer ranging from 25 to 110, and m represents an integer ranging from 13 to 55.

The nanoparticle according to one exemplary embodiment of the present invention forms a self-assembly or a self-aggregate by means of the balance between the positive charges and the negative charges. Also, as the amide bond specifically cleaves in a certain bioenvironment, the nanoparticle flows in cells, decomposes in a certain bioenvironment to deliver a carrier material, for example, a diagnostic reagent, an ATP reporter, a drug, or a gene into the cells. As a result, the nanoparticle may be used as a diagnostic or therapeutic drug or gene carrier. For example, the amide bond specifically cleaves by means of protons ($H^+$) in a pH range of 5.0 to 5.5 in cancer cells. As the amide bond cleaves, the nanoparticle may collapse to release the drug carried by the nanoparticle.

FIG. 1 is a diagram showing the action mechanisms of a prior-art nanocarrier and a nanocarrier according to one exemplary embodiment of the present invention so as to diagnose or treat cancer, and FIG. 2 is a diagram showing the structure of the bioenvironment-sensitive nanoparticle according to one exemplary embodiment of the present invention (an upper panel), and the inflow of the bioenvironment-sensitive nanoparticle according to one exemplary embodiment of the present invention into cells and the selective collapse of the bioenvironment-sensitive nanoparticle in tumor microenvironment (a lower panel). Here, the bioenvironment-sensitive nanoparticle flows in cancer cells, and then selectively collapses as an acid radical having a negative charge is separated from the nanoparticle in an intrinsic acidic environment in the cancer cells.

According to one exemplary embodiment, the hydrophilic polymer may include at least one selected from the group consisting of polyalkylene glycol, polyethylene oxide, polyoxazoline, poly(N-vinylpyrrolidone), polyvinyl alcohol, polyhydroxyethyl methacrylate, dextran, poly-L-serine, poly-L-threonine, poly-L-tyrosine, poly-L-lysine, poly-L-arginine, poly-L-histidine, poly-L-aspartic acid, and poly-L-glutamic acid, which may be used alone or in combination of two or more. For example, a polyalkylene glycol having a molecular weight of 1000 to 5000, or a derivative thereof may be used. Also, a methoxy amino polyethylene glycol having a molecular weight of 1000 to 5000 may also be used.

The hydrophilic polymer may be properly modified using known technology to form a bond to a polymer having positive charges, or a polymer containing a functional group capable of forming an amide bond. For example, the mPEG-NH$_2$ undergoes a modification process of mPEG-OH→mPEG-TsCl→mPEG-N3→mPEG-NH$_2$, and then may be used in the form of mPEG-NH$_2$.

According to one exemplary embodiment, the polymer having positive charges, or the polymer containing the functional group capable of forming the amide bond may include, but is not limited to, basic amino acids. For example, the polymer may be at least one selected from the group consisting of poly-L-lysine, poly-L-histidine, and poly-L-arginine. For example, the polymer having positive charges may be a lysine homopolymer.

Also, the polymer having positive charges, or the polymer containing the functional group capable of forming the amide bond may be represented by the following Formula 3.

(poly-M)$k$ [Formula 3]

In Formula 3, M represents lysine, histidine, or arginine, and k represents an integer ranging from 10 to 100.

According to one exemplary embodiment, the acid radical may be a succinyl radical ($-CO-CH_2-CH_2-COO^-$).

The block copolymer (II) into which the succinyl radical is introduced may be synthesized by reacting succinyl chloride with the block copolymer (I) containing the hydrophilic polymer and the polymer having positive charges. Such a block copolymer (I) is negatively charged due to the presence of the succinyl radical.

According to one exemplary embodiment, the bioenvironment-sensitive nanoparticle may be in the form of a micelle or a polymersome. In the present invention, the shape of the micelle refers to a shape of a spherical particle having a hydrophilic core and a hydrophilic shell. The shape of the polymersome refers to a structure in which a hydrophilic shell having charges and a hydrophilic shell having no charges doubly surround a hollowed hydrophilic core.

Such a shape of the nanoparticle may be altered according to the mass fraction of the hydrophilic polymer, as calculated by the following Equation 1. For example, when the mass fraction of the hydrophilic polymer is in a range of 25 to 40, the nanoparticle is in the form of a polymersome.

Mass fraction=Molecular weight of Hydrophilic polymer/(Molecular weight of Hydrophilic polymer+Molecular weight of Polymer having positive charges or Polymer to which acid radical having negative charge is bound via amide bond). [Equation 1]

Also, when the mass fraction of the hydrophilic polymer is greater than 40 and less than or equal to 70 as calculated by Equation 1, the nanoparticle is in the form of a micelle.

According to one exemplary embodiment, the nanoparticle may further include a pharmaceutical active ingredient. The pharmaceutical active ingredient may be physicochemically impregnated or bound in a hydrophilic domain. In the micelle or polymersome structure, a hydrophilic material may be carried in the hollowed hydrophilic core. Therefore, the nanoparticle according to one exemplary embodiment of the present invention may be used as a drug carrier since the nanoparticle may carry a hydrophilic drug, gene, and the like.

The pharmaceutical active ingredient may include, but is not limited to, an anticancer agent, an antibiotic, a hormone, a hormone antagonist, an interleukin, an interferon, a growth factor, a tumor necrosis factor, an endotoxin, a lymphotoxin, a urokinase, a streptokinase, a tissue plasminogen activator, a protease inhibitor, an alkyl phosphocholine, a radioisotope-labeled component, a cardiovascular system drug, a gastrointestinal system drug, and a nervous system drug, which may be used alone or in combination of two or more.

For example, the nanoparticle may further include an ATP reporter. The ATP reporter refers to a substance that binds to ATP to form a color. In this case, a level of the ATP may be analyzed by detecting a degree of color formation using an ATP reporter. The ATP reporter is well known in the related art, and known ATP reporters may be used without limitation. For example, the ATP reporter may include poly(1-(3-((4-methylthiophen-3-yl)oxy)propyl) quinuclidin-1-ium, and the like.

Also, the nanoparticle according to one exemplary embodiment of the present invention may further include a fluorescent material. Here, the fluorescent material may be used for diagnosis of disease. The fluorescent material may be physicochemically impregnated or bound in a hydrophilic domain. The fluorescent material may be a phosphor emitting fluorescence in a visible ray or near-infrared ray region. For example, fluorescein, BODYPY, tetramethylrhodamine, Alexa, Cyanine, allophycocyanin, or other fluorescent materials emitting fluorescence may be used as the fluorescent material. Also, fluorescent materials having a high quantum yield may be used. Also, the fluorescent material may be a hydrophilic dye.

The present invention also provides a method of manufacturing the above-described bioenvironment-sensitive nanoparticle, which includes reacting a block copolymer (I) and a block copolymer (II). Here, the block copolymer (I) contains a hydrophilic polymer and a polymer having positive charges as repeating units, the block copolymer (II) contains a hydrophilic polymer and a polymer, to which an acid radical having a negative charge is bound via an amide bond, as repeating units, and the polymer to which the acid radical having a negative charge is bound via the amide bond contains a polymer containing a functional group capable of forming an amide bond, and an acid radical having a negative charge bound thereto via the amide bond.

The bioenvironment-sensitive nanoparticle according to one exemplary embodiment of the present invention is generally composed of a block copolymer (I) having positive charges, and a block copolymer (II) having negative charges. The block copolymer (I) contains a hydrophilic polymer and a polymer having positive charges as repeating units. In the case of the block copolymer (I), for example, a methoxy amino polyethylene glycol-poly-L-lysine block copolymer may be prepared by reacting a lysine-N-carboxy-anhydride (Lys-NCA) with methoxy amino polyethylene glycol (mPEG-NH$_2$) (see Schemes 1 and 2).

Here, the block copolymer (I) may react with succinyl chloride to prepare the block copolymer (II) having negative charges. The block copolymer (II) contains a hydrophilic polymer and a polymer, to which an acid radical having a negative charge is bound via an amide bond, as repeating units. The polymer to which the acid radical having a negative charge is bound via the amide bond contains a polymer containing a functional group capable of forming an amide bond, and an acid radical having a negative charge bound thereto via the amide bond.

The block copolymer (I) containing the hydrophilic polymer and the polymer having positive charges, and the block copolymer (II) having negative charges prepared by reacting succinyl chloride with the block copolymer (I) may react at a proper weight ratio to prepare a bioenvironment-sensitive nanoparticle. For example, the block copolymers (I) and (II) may react at a weight ratio of 10:90 to 90:10, 40:60 to 60:40, or 50:50. For example, such a method includes a method of directly dispersing a block copolymer having positive charges and negative charges in an aqueous solution and applying ultrasonic waves to the resulting dispersion, a method of dispersing or dissolving a block copolymer having positive charges and negative charges in an organic solvent and extracting or evaporating the organic solvent with an excessive amount of water, a method of dispersing or dissolving a block copolymer having positive charges and negative charges in an organic solvent and dialyzing the resulting dispersion with an excessive amount of water, and a method of dispersing or dissolving a block copolymer having positive charges and negative charges in an organic solvent and intensely evaporating the solvent in a homogenizer or a high-pressure emulsifier. According to the following exemplary embodiments, the block copolymer having positive charges and negative charges is dispersed in an aqueous solution, and vortexed to prepare a nanoparticle in the form of a polymersome.

The organic solvent that may be used herein may include chloroform, hexane, heptane, methylene chloride, benzene, toluene, tetrahydrofuran, acetone, or a mixture thereof, but the present invention is not limited thereto.

The average particle diameter of the nanoparticle thus prepared may be less than or equal to 200 nm, but the present invention is not limited thereto. For example, the average particle diameter of the nanoparticle may be in a range of 50 to 200 nm. Within this particle diameter range, the nanoparticle has an advantage in that it has excellent bioavailability.

Also, the present invention provides a pharmaceutical use of the bioenvironment-sensitive nanoparticle. According to one exemplary embodiment, the bioenvironment-sensitive nanoparticle may be used as a drug carrier or a target-directed contrast agent composition together with a pharmaceutically available carrier.

The nanoparticle according to one exemplary embodiment of the present invention is specifically sensitized in a certain bioenvironment. For example, the amide bond included in the nanoparticle has a characteristic of cleaving only in a specific endosomal bioenvironment (pH 5.0 to 5.5) of cancer cells. As the amide bond cleaves, the acid radical is separated from the nanoparticle. As a result, the nanoparticle decomposes. Also, since the conventional nanoparticles using a hydrophobic interaction have a relatively weak binding affinity, the conventional nanoparticles are affected by extracellular enzymes, and the like, resulting in a non-specific reaction. On the other hand, the nanoparticle according to one exemplary embodiment of the present invention has a relatively strong binding affinity such as ionic bonds, and thus is stable since non-specific interactions do not occur in an environment out of cancer cells. Therefore, the nanoparticle according to one exemplary embodiment of the present invention may target cancer cells, and thus may be used as a contrast agent capable of imaging a target region using a magnetic resonance device and an optical imaging device.

Therefore, the amphiphilic nanoparticle according to one exemplary embodiment of the present invention may be used to diagnose and/or treat various diseases associated with a tumor, for example, squamous cell carcinoma, uterine cancer, uterine cervical cancer, prostate cancer, head and neck cancer, pancreatic cancer, brain cancer, breast cancer, liver cancer, skin cancer, esophageal cancer, testicular cancer, renal cancer, colon cancer, rectal cancer, gastric cancer, bladder cancer, ovarian cancer, bile duct cancer, and gallbladder cancer.

The pharmaceutically available carrier includes carriers and vehicles generally used in the field of medicine. Specifically, the pharmaceutically available carrier includes at least one selected from the group consisting of an ion exchange resin, alumina, aluminum stearate, lecithin, a serum protein (for example, human serum albumin), a buffer (for example, various phosphates, glycine, sorbic acid, potassium sorbate, and a partial glyceride mixture of saturated vegetable fatty acid), water, a salt or electrolyte (for example, protamine sulfate, disodium hydrogen phosphate, potassium hydrogen phosphate, sodium chloride, and zinc salt), colloidal silica, magnesium trisilicate, polyvinylpyrrolidone, cellulose-based substrate, polyethylene glycol, sodium carboxymethylcellulose, a polyacrylate, wax, polyethylene glycol, and wool fat, but the present invention is not limited thereto.

Also, the target-directed contrast agent composition according to one exemplary embodiment of the present invention may further include a lubricating agent, a wetting agent, an emulsifying agent, a suspending agent, or a preservative in addition to the components.

According to one exemplary embodiment, the target-directed contrast agent composition of the present invention may be prepared as a water-soluble solution for parenteral administration. Preferably, a Hank's solution, a Ringer's solution, or a buffer solution such as physically buffered saline may be used as the target-directed contrast agent composition. A substrate capable of enhancing the viscosity of a suspension, such as sodium carboxymethylcellulose, sorbitol, or dextran, may be added to a water-soluble injectable suspension.

Another preferred aspect of the target-directed contrast agent composition according to one exemplary embodiment of the present invention may be in the form of a sterile injectable formulation of a sterile injectable aqueous or oily suspension. Such a suspension may be formulated according to known techniques known in the related art using a proper dispersing or wetting agent (for example, Tween 80), and a suspending agent.

Also, the sterile injectable formulation may be a sterile injectable solution or suspension in a non-toxic parenterally available diluent or solvent (for example, a solution in 1,3-butanediol). The vehicle and solvent that may be used herein includes mannitol, water, a Ringer's solution, and an isotonic sodium chloride solution. Also, sterile non-volatile oil is generally used as a solvent, or a suspending medium. Any less-irritant, non-volatile oil may be used as long as it includes a synthetic mono- or di-glyceride for this purpose.

The target-directed contrast agent composition according to one exemplary embodiment of the present invention may be administered into tissues or cells isolated from a subject to be diagnosed, and then used to detect signals emitted by the nanoparticle and obtain images.

Magnetic resonance imaging (MRI) and optical imaging are preferably used to detect the signals emitted by the nanoparticle.

The bioenvironment-sensitive nanoparticle according to one exemplary embodiment of the present invention may also be used to analyze the activity or quantity of ATP. As described above, when the ATP reporter is carried by the nanoparticle, the succinyl radical is separated from the nanoparticle due to the collapse of the amide bond in the cancer cells. As a result, the nanoparticle decomposes to release the ATP reporter. Thus, the ATP reporter is transferred into the cancer cells, and a degree of color formation of the ATP reporter differs according to the quantity of ATP present in the cancer cells. Therefore, the activity or quantity of ATP may be detected by measuring the degree of color formation of the ATP reporter. Since ATP is rich in the cancer cells, cancer may be diagnosed by analyzing the activity of ATP in the cancer cells.

Therefore, the present invention provides a method of analyzing the activity or quantity of ATP, which includes treating a test sample with the bioenvironment-sensitive nanoparticle, and measuring the activity or quantity of ATP. Also, the present invention provides a method of diagnosing cancer, which includes treating a test sample with the bioenvironment-sensitive nanoparticle, and measuring the activity or quantity of ATP to analyze the activity or quantity of ATP.

According to one exemplary embodiment, the test sample may be cells, or tissues, but the present invention is not limited to.

Hereinafter, the present invention will be described in detail with reference to Examples and Experimental Examples. However, it should be understood that the detailed description proposed herein is merely a preferable example for the purpose of illustrations only, not intended to limit the scope of the invention.

EXAMPLES

Example 1

Preparation of Bioenvironment-Sensitive Nanoparticle (1) Preparation of Hydrophilic Block Copolymer Having Positive Charges and Negative Charges.

A block copolymer, which included methoxy amino polyethylene glycol (mPEG-NH$_2$) having a molecular weight of 2000, and poly-L-lysine that was a hydrophilic polyamino acid, and had positive charges, and a block copolymer of methoxy amino polyethylene glycol, poly-L-lysine, and succinyl chloride, which was synthesized by reacting succinyl chloride with the block copolymer, and had negative charges were synthesized as hydrophilic polymers (FIG. 2).

mPEG-OH was modified into mPEG-NH$_2$. The modification process was performed in the order of mPEG-OH→mPEG-TsCl→mPEG-N$_3$→mPEG-NH$_2$, as represented by the following Scheme 1.

[Scheme 1]

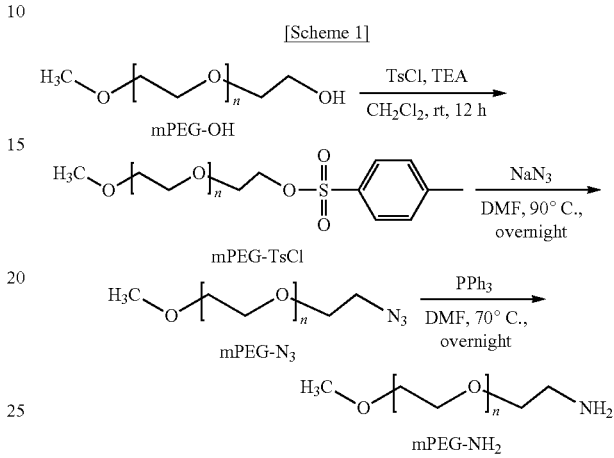

The modification was confirmed using FT-IR and NMR. As shown in FIG. 3, it was revealed that the modification was made by locating CH$_3$ of mPEG at 2,850 cm$^{-1}$, S—O of mPEG-TsCl at 560 cm$^{-1}$, and N$_3$ of mPEG-N$_3$ at 2,103 Cm$^{-1}$ using FT-IR. As shown in FIG. 4, it was also revealed that the modification was made by locating 2H of mPEG-TsCl at 7.79 and 7.49 ppm, and CH$_2$ of mPEG-NH$_2$ at 2.90 ppm using NMR. The characteristics of the modified mPEG-NH$_2$ are listed in the following Table 1.

TABLE 1

| Sample | Yield (%) | Conversion rate (%) | Molar mass (g/mol) GPC | $^1$H-NMR |
|---|---|---|---|---|
| mPEG$_{2000}$ | — | 100 | 2,000 | — |
| mPEG-TsCl | 92 | 92 | 1,963 | 1,972 |
| mPEG-N$_3$ | 86 | 97 | 1,985 | 1,996 |
| mPEG-NH$_2$ | 92 | 99 | 1,990 | 2,012 |

To synthesize poly-L-lysine, lysine-N-carboxyanhydride (Lys-NCA) was synthesized by a Fuchs-Farthing method using triphosgene. Specifically, to prepare Lys-NCA, L-lysine was dissolved at 40° C. in THF under a nitrogen atmosphere, and triphosgene was added thereto. After 3 hours, Lys-NCA obtained by precipitation in n-hexane was recrystallized from THF/n-hexane. When the Lys-NCA was prepared, the Lys-NCA was added to a DMF solution of mPEG-NH$_2$, and the left at 35° C. for 24 hours under a nitrogen atmosphere to synthesize mPEG-b-poly-L-lysine (mPEG-b-pLys). This procedure is shown in the following Scheme 2.

[Scheme 2]

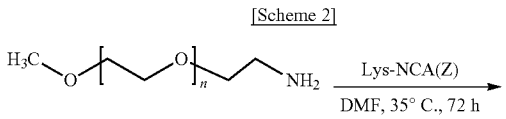

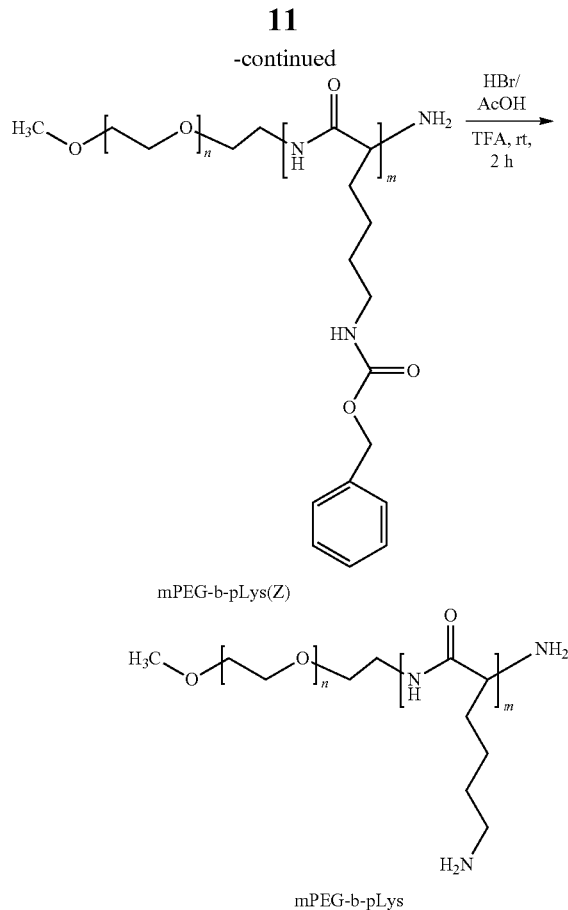

mPEG-b-pLys(Z)

mPEG-b-pLys

The block copolymer synthesized by precipitation in diethyl ether was separated. Then, the block copolymer was deprotected to remove a Z group of the synthesized mPEG-b-pLys. Trifluoroacetic acid (TFA) and HBr were added to the synthesized block copolymer. The product thus obtained was separated by dialysis for 24 hours, and freeze-dried.

It was confirmed whether the polymerized product was mPEG-b-pLys using FT-IR. As a result, it could be seen that the modification was made by locating $CH_3$ of mPEG at 2,850 $cm^{-1}$, amide I of Lys-NCA at 1,650 $cm^{-1}$, and Z of mPEG-b-pLys(Z) at 1,710 $cm^{-1}$, as shown in FIG. 5.

To obtain mPEG-b-dPLL having negative charges, the synthesized product, mPEG-b-pLys, was dissolved in a PBS buffer (pH 8.5), and succinyl chloride was added thereto, and stirred for 24 hours. The resulting product was separated by dialysis for 24 hours in a PBS buffer (pH 7.4), and then freeze-dried.

(2) Formation of Polymersome of Synthesized Product

A polymersome formed of the block copolymer having positive charges and negative charges was prepared. The positively charged block copolymer, mPEG-b-aPLL, and the negatively charged block copolymer, mPEG-b-dPLL, were dispersed in an aqueous phase at a ratio of 50:50, and then vortexed for 6 hours. As a result, the polymersome formed of the block copolymer having positive charges and negative charges was obtained.

Experimental Example 1

Determination of Formation of Bioenvironment-Sensitive Nanoparticle

The shape of the bioenvironment-sensitive nanoparticle prepared in Example 1 was confirmed on TEM and SEM images. As a result, it could be seen that the bioenvironment-sensitive nanoparticle had a polymersome structure in which a hydrophilic shell having charges and a hydrophilic shell having no charges doubly surrounded a hollowed hydrophilic core, as shown in FIG. 6.

Experimental Example 2

Determination of Cytotoxicity Effect of Bioenvironment-Sensitive Nanoparticle

Anticancer effects when only a drug was delivered and when the drug carried by the bioenvironment-sensitive nanoparticle according to one exemplary embodiment of the present invention was delivered were comparatively analyzed. A cytotoxicity test was performed in biliary tract cancer cell lines ASPC and Hucct-1 using doxorubicin (DOX, 200 mM) as the drug. As a result, it was revealed that the bioenvironment-sensitive nanoparticle according to one exemplary embodiment of the present invention had an excellent cytotoxicity effect even when used at a lesser concentration, compared to when only the drug was delivered, as shown in FIG. 7.

The results indicated that the nanoparticle according to one exemplary embodiment of the present invention was able to efficiently deliver the drug.

Experimental Example 3

Determination of Inflow of Bioenvironment-Sensitive Nanoparticle into Cells

The inflow of the bioenvironment-sensitive nanoparticle prepared in Example 1 into the cells was confirmed using the biliary tract cancer cell lines ASPC and Hucct-1. The results obtained after the bioenvironment-sensitive nanoparticle was allowed to flow in the cell for 4 hours are shown in FIG. 8. Blue fluorescence represents that the cells were stained with Hoechst 33258, and green fluorescence represents that the cells were stained with FITC-Dextran.

As a result, it could be seen that the bioenvironment-sensitive nanoparticle according to one exemplary embodiment of the present invention effectively flew in the cells.

The present invention has been described in detail. However, it should be understood that the detailed description and specific examples, while indicating preferred embodiments of the invention, are given by way of illustration only, since various changes and modifications within the scope of the invention will become apparent to those skilled in the art from this detailed description.

What is claimed is:

1. A bioenvironment-sensitive nanoparticle comprising a block copolymer (I) having positive charges, and a block copolymer (II) having negative charges,
   wherein the block copolymer (I) contains a hydrophilic polymer and a polymer having positive charges as repeating units;
   the block copolymer (II) contains a hydrophilic polymer and a polymer, to which an acid radical having a negative charge is bound via an amide bond, as repeating units;
   the polymer to which the acid radical having a negative charge is bound via the amide bond contains a polymer containing a functional group capable of forming an amide bond, and an acid radical having a negative charge bound thereto via the amide bond;

the block copolymers (I) and (II) form a self-assembly by means of the balance between the positive charges and the negative charges; and the block copolymers (I) and (II) comprise only hydrophilic polymers as a repeating unit and do not comprise hydrophobic polymers as a repeating unit, and wherein the nanoparticle is in the form of a polymersome in which a mass fraction of the hydrophilic polymer is in a range of 25 to 40, as calculated according to the following Equation 1:

Mass fraction=Molecular weight of Hydrophilic polymer/(Molecular weight of Hydrophilic polymer+Molecular weight of Polymer having positive charges or Polymer to which acid radical having negative charge is bound via amide bond).

2. The nanoparticle of claim 1, wherein the amide bond in the nanoparticle cleaves in a pH range of 5.0 to 5.5 in cancer cells.

3. The nanoparticle of claim 1, wherein the hydrophilic polymer of any of said block copolymers (I) and (II) independently comprises least one selected from the group consisting of polyalkylene glycol, polyethylene oxide, polyoxazoline, poly(N-vinylpyrrolidone), polyvinyl alcohol, polyhydroxyethyl methacrylate, dextran, poly-L-serine, poly-L-threonine, poly-L-tyrosine, poly-L-lysine, poly-L-arginine, poly-L-histidine, poly-L-aspartic acid, and poly-L-glutamic acid.

4. The nanoparticle of claim 1, wherein the hydrophilic polymer of any of said block copolymers (I) and (II) is methoxy amino polyethylene glycol.

5. The nanoparticle of claim 1, wherein the polymer having positive charges, or the polymer containing the functional group capable of forming the amide bond comprises at least one selected from the group consisting of poly-L-lysine, poly-L-histidine, and poly-L-arginine.

6. The nanoparticle of claim 1, wherein the acid radical is a succinyl radical.

7. The nanoparticle of claim 1, wherein the nanoparticle has an average particle diameter of 50 to 200 nm.

8. A bioenvironment-sensitive nanoparticle comprising a block copolymer (I) having positive charges, and a block copolymer (II) having negative charges, wherein the block copolymer (I) contains a hydrophilic polymer and a polymer having positive charges as repeating units;

the block copolymer (II) contains a hydrophilic polymer and a polymer, to which an acid radical having a negative charge is bound via an amide bond, as repeating units;

the polymer to which the acid radical having a negative charge is bound via the amide bond contains a polymer containing a functional group capable of forming an amide bond, and an acid radical having a negative charge bound thereto via the amide bond;

the block copolymers (I) and (II) form a self-assembly by means of the balance between the positive charges and the negative charges; and the block copolymers (I) and (II) comprise only hydrophilic polymers as a repeating unit and do not comprise hydrophobic polymers as a repeating unit, and wherein the nanoparticle is in the form of a micelle in which the mass fraction of the hydrophilic polymer is greater than 40 and less than or equal to 70, as calculated according to the following Equation 1:

Mass fraction=Molecular weight of Hydrophilic polymer/(Molecular weight of Hydrophilic polymer+Molecular weight of Polymer having positive charges or Polymer to which acid radical having negative charge is bound via amide bond).

9. The nanoparticle of claim 1, wherein the nanoparticle further comprises a pharmaceutical active ingredient.

10. The nanoparticle of claim 1, wherein the nanoparticle further comprises a fluorescent material.

11. The nanoparticle of claim 1, wherein the nanoparticle further comprises an ATP reporter.

12. The nanoparticle of claim 11, wherein the ATP reporter is poly(1-(3-((4-methylthiophen-3-yl)oxy)propyl)quinuclidin-1-ium.

13. A method of manufacturing the bioenvironment sensitive nanoparticle defined in claim 1, comprising:

reacting a block copolymer (I) and a block copolymer (II), wherein the block copolymer (I) contains a hydrophilic polymer and a polymer having positive charges as repeating units;

the block copolymer (II) contains a hydrophilic polymer and a polymer, to which an acid radical having a negative charge is bound via an amide bond, as repeating units; and the block copolymers (I) and (II) comprise only hydrophilic polymers as a repeating unit and do not comprise hydrophobic polymers as a repeating unit; and the polymer to which the acid radical having a negative charge is bound via the amide bond contains a polymer containing a functional group capable of forming an amide bond, and an acid radical having a negative charge bound thereto via the amide bond; and the nanoparticle is in the form of a polymersome in which a mass fraction of the hydrophilic polymer is in a range of 25 to 40, as calculated according to the following Equation 1:

Mass fraction=Molecular weight of Hydrophilic polymer/(Molecular weight of Hydrophilic polymer+Molecular weight of Polymer having positive charges or Polymer to which acid radical having negative charge is bound via amide bond).

14. The nanoparticle of claim 8, wherein the hydrophilic polymer of any of said block copolymers (I) and (II) independently comprises least one selected from the group consisting of polyalkylene glycol, polyethylene oxide, polyoxazoline, poly(N-vinylpyrrolidone), polyvinyl alcohol, polyhydroxyethyl methacrylate, dextran, poly-L-serine, poly-L-threonine, poly-L-tyrosine, poly-L-lysine, poly-L-arginine, poly-L-histidine, poly-L-aspartic acid, and poly-L-glutamic acid.

15. The nanoparticle of claim 8, wherein the hydrophilic polymer of any of said block copolymers (I) and (II) is methoxy amino polyethylene glycol.

16. The nanoparticle of claim 8, wherein the polymer having positive charges, or the polymer containing the functional group capable of forming the amide bond comprises at least one selected from the group consisting of poly-L-lysine, poly-L-histidine, and poly-L-arginine.

17. The nanoparticle of claim 8, wherein the acid radical is a succinyl radical.

18. The nanoparticle of claim 8, wherein the nanoparticle has an average particle diameter of 50 to 200 nm.

19. The nanoparticle of claim 8, wherein the nanoparticle further comprises a pharmaceutical active ingredient.

20. The nanoparticle of claim 8, wherein the nanoparticle further comprises an ATP reporter.

21. The nanoparticle of claim 20, wherein the ATP reporter is poly(1-(3-((4-methylthiophen-3-yl)oxy)propyl) quinuclidin-1-ium.

22. The nanoparticle of claim 8, wherein the nanoparticle further comprises a fluorescent material.

23. A method of manufacturing the bioenvironment-sensitive nanoparticle defined in claim 8, comprising:
   reacting a block copolymer (I) and a block copolymer (II),
   wherein the block copolymer (I) contains a hydrophilic polymer and a polymer having positive charges as repeating units;
   the block copolymer (II) contains a hydrophilic polymer and a polymer, to which an acid radical having a negative charge is bound via an amide bond, as repeating units;
   the polymer to which the acid radical having a negative charge is bound via the amide bond contains a polymer containing a functional group capable of forming an amide bond, and an acid radical having a negative charge bound thereto via the amide bond; and
   the block copolymers (I) and (II) comprise only hydrophilic polymers as a repeating unit and do not comprise hydrophobic polymers as a repeating unit; and
   the nanoparticle is in the form of a polymersome in which a mass fraction of the hydrophilic polymer is in a range of 25 to 40, as calculated according to the following Equation 1:

Mass fraction=Molecular weight of Hydrophilic polymer/(Molecular weight of Hydrophilic polymer+Molecular weight of Polymer having positive charges or Polymer to which acid radical having negative charge is bound via amide bond).

* * * * *